United States Patent
Brehm et al.

[11] Patent Number: 6,053,729
[45] Date of Patent: Apr. 25, 2000

[54] UNITARY SUBSTANTIALLY NICKEL FREE ALLOY INJECTION MOLDED ORTHODONTIC BRACKET

[75] Inventors: Lindsay W. Brehm, Encinitas; Stephen M. Huff; Chhattar S. Kucheria, both of San Diego, all of Calif.

[73] Assignee: Ortho Corporation, San Marcos, Calif.

[21] Appl. No.: 09/033,370

[22] Filed: Mar. 2, 1998

[51] Int. Cl.[7] .................................................. A61L 3/00
[52] U.S. Cl. ...................................... 433/9; 433/8; 433/17
[58] Field of Search ....................................... 433/8, 9, 17

[56] References Cited

U.S. PATENT DOCUMENTS

| | | | |
|---|---|---|---|
| D. 340,523 | 10/1993 | Barngrover | D24/180 |
| D. 383,844 | 9/1997 | Kelly | D24/180 |
| 3,865,585 | 2/1975 | Rademacher | 420/436 |
| 4,243,386 | 1/1981 | Kawaguchi | 433/9 |
| 4,430,061 | 2/1984 | Webb et al. | 433/9 |
| 4,514,359 | 4/1985 | Andrews | 420/436 |
| 4,820,151 | 4/1989 | Pospisil | 433/17 |
| 4,878,840 | 11/1989 | Reynolds | 433/9 |
| 4,927,362 | 5/1990 | Snead | 433/17 |
| 5,022,854 | 6/1991 | Broughton et al. | 433/8 |
| 5,039,574 | 8/1991 | Kulmburg | 428/433 |
| 5,154,606 | 10/1992 | Wildman | 433/8 |
| 5,227,131 | 7/1993 | Weigand | 420/436 |
| 5,254,002 | 10/1993 | Reher et al. | 433/8 |
| 5,263,858 | 11/1993 | Yoshida et al. | 433/8 |
| 5,267,854 | 12/1993 | Schmitt | 433/8 |
| 5,292,248 | 3/1994 | Schultz | 433/8 |
| 5,374,187 | 12/1994 | Vashi | 433/8 |
| 5,378,146 | 1/1995 | Sterrett | 433/11 |
| 5,380,196 | 1/1995 | Kelly et al. | 433/8 |
| 5,383,784 | 1/1995 | Sernetz | 433/7 |
| 5,474,448 | 12/1995 | Andreiko et al. | 433/24 |
| 5,511,976 | 4/1996 | Wildman | 433/10 |
| 5,529,491 | 6/1996 | Hilgenfeldt et al. | 433/23 |
| 5,556,277 | 9/1996 | Yawata et al. | 433/17 |
| 5,595,484 | 1/1997 | Orikasa et al. | 433/8 |
| 5,597,302 | 1/1997 | Pospisil et al. | 433/8 |
| 5,613,849 | 3/1997 | Tanaka et al. | 433/8 |
| 5,622,494 | 4/1997 | Andreiko et al. | 433/9 |

*Primary Examiner*—John J. Wilson
*Assistant Examiner*—Patrick A. Hilsmier
*Attorney, Agent, or Firm*—Fulwider Patton Lee & Utecht, LLP

[57] ABSTRACT

The orthodontic appliance is metal injection molded as a unitary bracket, and is a made of a Stellite cobalt chromium alloy composition formulated to be substantially nickel-free, containing less than 1% nickel, in order to alleviate nickel allergic reactions experienced by a small fraction of the population to nickel. While nickel improved hardness of the bracket, the elements of chromium and molybdenum in the proposed alloy for the bracket also contribute to hardness of the alloy. The orthodontic bracket comprises a unitary metal injection molded body including a bonding base adapted to adhere to a tooth surface, and an archwire slot adapted for receiving an archwire. The preferred composition consists essentially of 59–69% by weight cobalt, 26–30% by weight chromium, 4–8% by weight molybdenum, and 2% or less by weight trace elements. The bonding base has a bottom base pattern in the form of a plurality of rectangular or square pockets that are approximately 0.005 to 0.015 inch in size. In another embodiment, the orthodontic appliance can also have a facebow tube, a primary archwire slot, and an auxiliary archwire slot. In another currently preferred aspect, the primary archwire slot includes an auxiliary archwire slot, and tiewings. The tube can have a round aperture for receiving a cylindrical wire, or a rectangular aperture for receiving an archwire.

17 Claims, 2 Drawing Sheets

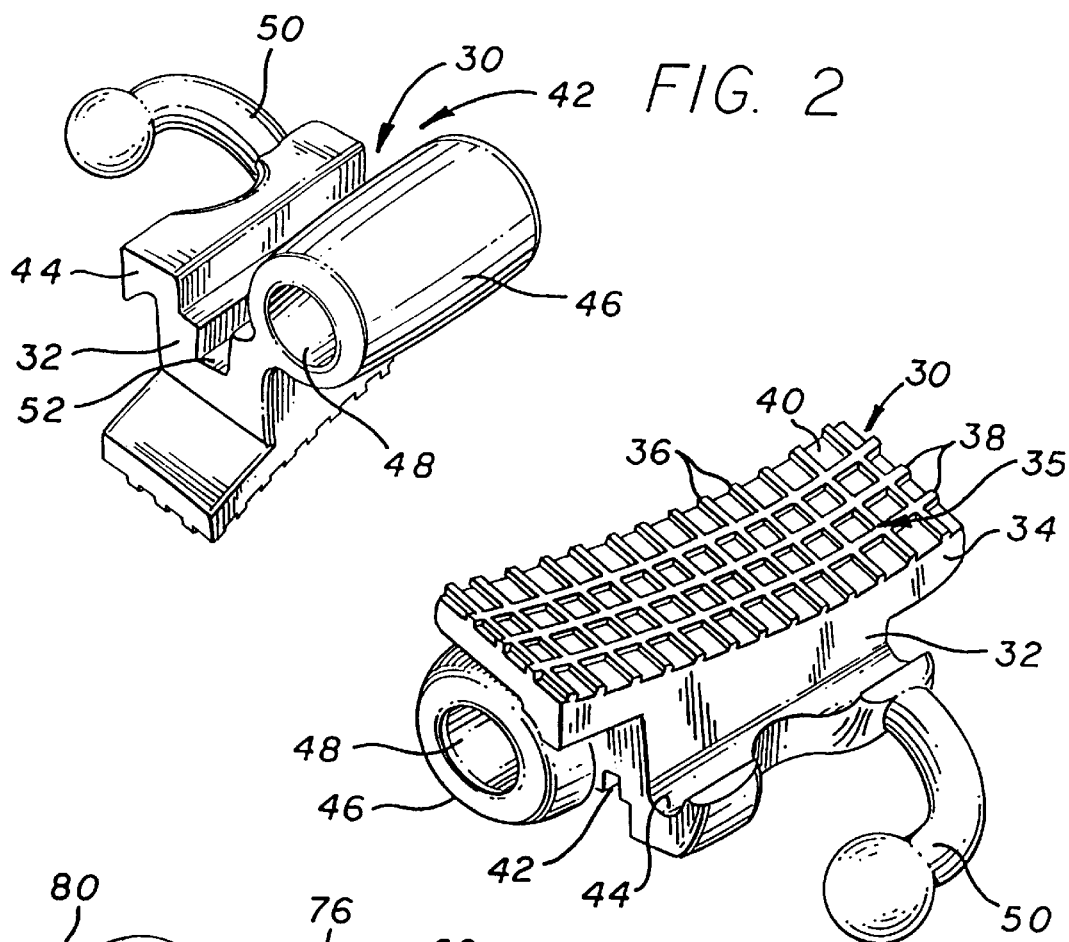
FIG. 2
FIG. 3
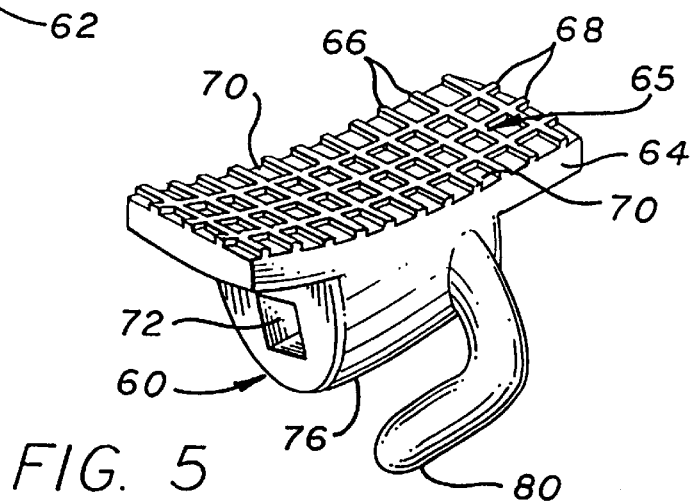
FIG. 4
FIG. 5

UNITARY SUBSTANTIALLY NICKEL FREE ALLOY INJECTION MOLDED ORTHODONTIC BRACKET

BACKGROUND OF THE INVENTION

1. Field of the Invention

This invention relates generally to orthodontic appliances, and more particularly concerns unitary metal injection molded orthodontic brackets made of a nickel free metal alloy in order to alleviate nickel allergy reactions experienced by a small fraction of the population.

2. Description of Related Art

Orthodontic appliances, such as brackets, buccal tubes and the like, are typically applied to teeth by adhering the appliances to the surface of the teeth. Such appliances typically include archwire portions for receiving an archwire and ligature elastic bands to provide corrective forces to straighten and reposition the teeth. The orthodontic appliances include a base portion adapted to conform to the shape of the teeth to which they are applied. The orthodontic appliances are subjected to tension and other stresses that can cause weakening of the bonds of the appliances to the teeth, and distortions in the structure of the appliances. The appliances are also subjected to cleaning that can erode the adhesion between the appliances and the teeth to which they are bonded, and are further stressed by normal mastication, so that it is not uncommon for such appliances to break away from teeth after bonding.

While orthodontic brackets are frequently made of plastic, their strength can be increased by forming at least portions of them from metal. The metal portions are typically small, and can be made by metal injection molding as a unitary metal part that is bonded or welded to be integral with the bracket. Such bonding or welding is also subject to structural instability. One known orthodontic bracket that is metal injection molded to have a basic monoblock unitary construction includes a base with raised posts adapted for abutting the surface of the teeth. However, the posts are shaped into mushroom shaped buttons by cold working, which can distort the microstructure and mechanical properties of the raised posts that are involved with bonding to teeth. Cold working of such structures can also be relatively expensive and complicated. It would therefore be desirable to form a unitary orthodontic bracket by metal injection molding to provide greater definition of the complicated geometry of the bracket as well as a well-defined base pattern to provide for better adhesion to a tooth, and to make the bracket structurally more sound.

The metal alloys used for making orthodontic brackets typically include nickel, which provides the brackets with improved hardness. However, allergies to nickel are quite common, so that it would be desirable to form the bracket of an alloy composition that is formulated to qualify as nickel-free, containing less than 1% nickel, in order to alleviate allergic reactions to nickel. The present invention meets these needs.

SUMMARY OF THE INVENTION

Briefly, and in general terms, the present invention provides for an improved unitary metal injection molded orthodontic appliance that provides greater definition of the complicated geometry of the bracket as well as a well-defined base pattern that provides for better adhesion to a tooth, and makes the bracket structurally more sound. In addition, by making the unitary orthodontic appliance by metal injection molding, no secondary operations are required during the manufacturing process. The metal alloy composition of the orthodontic appliance is preferably a Stellite cobalt chromium alloy that is formulated to be substantially nickel-free, containing less than 1% nickel, in order to alleviate allergic reactions experienced by a small fraction of the population to nickel. While nickel improved hardness of the bracket, the trace element of carbon in conjunction with the elements of cobalt, chromium and molybdenum in the proposed alloy for the bracket also has significant effect on the hardness of the alloy.

In one preferred aspect, the invention accordingly provides for a unitary metal injection molded orthodontic bracket for straightening teeth. The orthodontic bracket comprises a unitary metal injection molded body including a bonding base adapted to adhere to a tooth surface, and an archwire slot adapted for receiving an archwire. The body is formed from a metal alloy having a composition consisting essentially of cobalt, chromium, and molybdenum, with nickel being present in an amount less than 1% by weight. In a currently preferred embodiment, the composition consists essentially of 59–69% by weight cobalt, 26–30% by weight chromium, 4–8% by weight molybdenum, and 2% or less by weight trace elements. The body also preferably includes a plurality of tiewings, and the bonding base has a bonding base pattern in the form of a plurality of rectangular or square pockets that are approximately 0.005 to 0.015 inch in size.

In another currently preferred embodiment, the unitary metal injection molded orthodontic appliance comprises a unitary metal injection molded body having a bonding base and a facebow tube for receiving wires for anchorage and straightening of the tooth. The body has a surface defining a primary archwire slot for receiving an archwire for anchorage and straightening of the tooth, and the body is formed from a metal alloy having a composition consisting essentially of cobalt, chromium, and molybdenum, with nickel being present in an amount less than 1% by weight. In a currently preferred embodiment, the composition consists essentially of 59–69% by weight cobalt, 26–30% by weight chromium, 4–8% by weight molybdenum, and 2% or less by weight trace elements. In another currently preferred aspect, the primary archwire slot includes an auxiliary archwire slot for receiving the archwire. The body also preferably includes a plurality of tiewings, and the bonding base has a bonding base pattern in the form of a plurality of rectangular or square pockets that are approximately 0.005 to 0.015 inch in size. In this embodiment, the orthodontic appliance is preferably adapted for application to first and second molar teeth, and is preferably a buccal tube bracket. The facebow tube can have a round aperture for receiving a cylindrical wire, or a rectangular aperture for receiving an archwire.

These and other aspects and advantages of the invention will become apparent from the following detailed description and the accompanying drawings, which illustrate by way of example the features of the invention.

BRIEF DESCRIPTION OF THE DRAWINGS

FIG. 2 is a top perspective of a second embodiment of an orthodontic appliance according to the principles of the invention;

FIG. 3 is a bottom perspective of the orthodontic appliance of FIG. 2;

FIG. 4 is a top perspective of a third embodiment of an orthodontic appliance according to the principles of the invention; and FIG. 5 is a bottom perspective of the orthodontic appliance of FIG. 4.

DETAILED DESCRIPTION OF THE PREFERRED EMBODIMENTS

Figure 1:
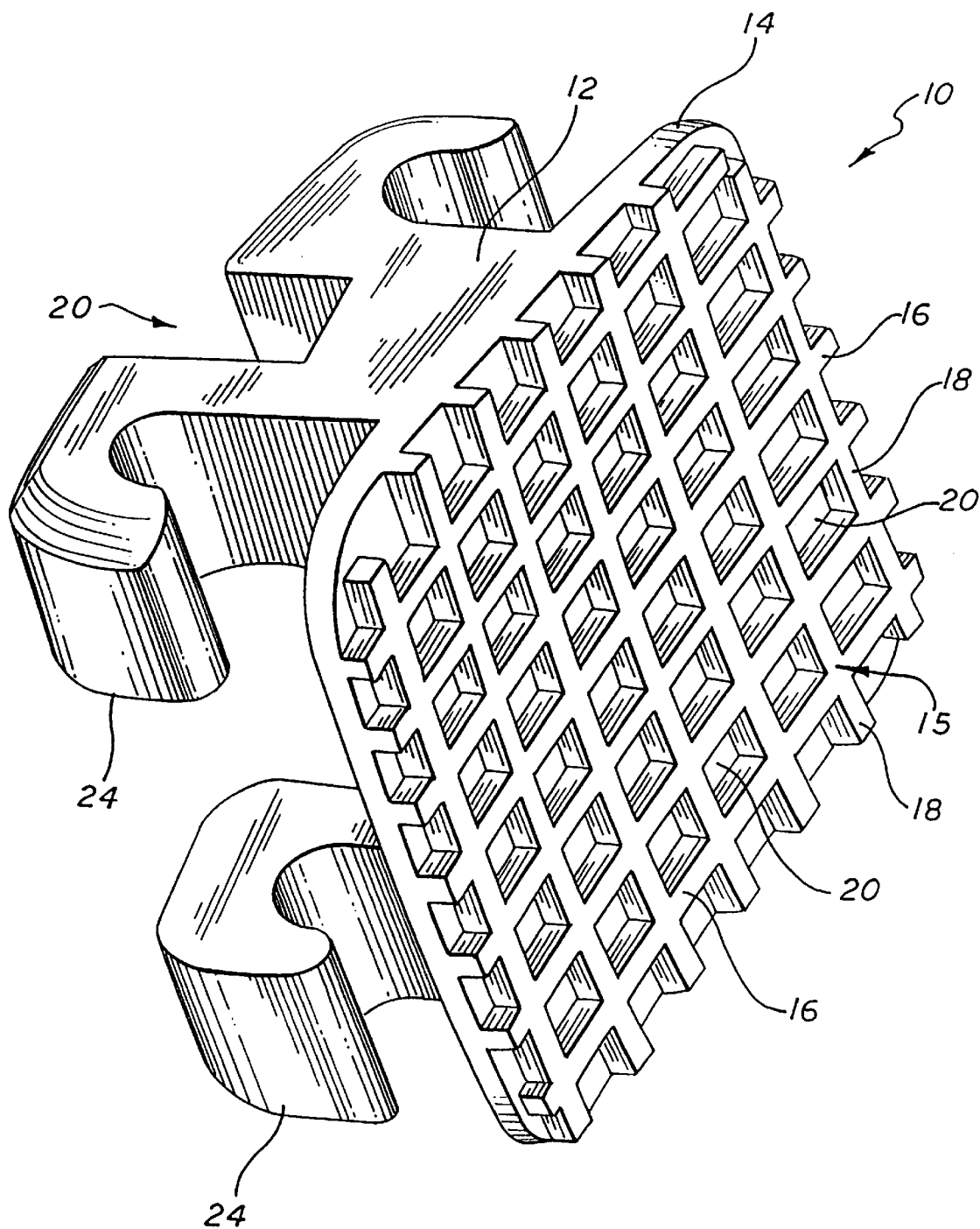
FIG. 1 is a bottom perspective view of an orthodontic bracket according to the principles of the invention.

Various stresses and strains from archwires, facebow wires, and mastication, as well as erosion from cleaning, can cause weakening of the bonds of orthodontic appliances to the teeth, and distortions in the structure of the appliances. Bonding or welding of portions of orthodontic appliances can also subject them to structural instability. While the hardness of metal alloy appliances can be improved by including nickel in the alloy composition, allergies to nickel are not uncommon.

As is illustrated in FIG. 1, in a first presently preferred embodiment, a unitary metal injection molded orthodontic bracket 10 for straightening teeth includes a metal injection molded unitary body 12 having a bonding base 14 that is adapted for use in adhering the bracket to a tooth surface (not shown). The bonding base is currently preferably formed to have a bottom rectangular grid 15 formed by cross-members 16, 18 intersecting at right angles, thereby forming a plurality of rectangular pockets 20. In a preferred aspect, the pattern on the bottom of the bonding base is in the form of a series of square or rectangular pockets that are typically approximately 0.005 to 0.015 inch in size along at least one side, and typically 0.005 inches deep at the centers of the pockets. The body also is also preferably formed to include an archwire slot 22 adapted for receiving an archwire, and a plurality of tiewings 24.

In a second presently preferred embodiment, illustrated in FIGS. 2 and 3, the orthodontic appliance is a unitary metal injection molded buccal tube 30 adapted for application to molars. The buccal tube includes a metal injection molded unitary body 32 having a unitary bonding base 34 with a rectangular grid 35 formed by cross-members 36,38 intersecting at right angles, forming a plurality of rectangular pockets 40 to improve adhesion to the tooth. In a preferred aspect, the pattern on the bottom of the bonding base is in the form of a series of square or rectangular pockets that are typically approximately 0.005 to 0.015 inch in size along at least one side, and typically 0.005 inches deep at the centers of the pockets. The unitary body includes a primary archwire slot 42 for receiving an archwire for anchorage and straightening of the tooth, and a plurality of tiewings 44 for ligature, such as with elastic bands. The unitary body also includes a facebow tube 46 having a round aperture 48 for receiving round wires to assist in anchorage and straightening of the tooth, along with the archwire. A hook 50 is also preferably provided on the unitary body, for attaching an elastic band, ligature wire, or the like. In a presently preferred aspect, the primary archwire slot also includes an auxiliary archwire slot 52 for receiving an archwire. The buccal tube 30 is typically used on the molar teeth, such as the molar, and second molar, for straightening and alignment.

With reference to FIGS. 4 and 5, in a third presently preferred embodiment, the orthodontic appliance is another type of a unitary metal injection molded buccal tube 60 for molars. The buccal tube has a metal injection molded unitary body 62 having a unitary bonding base 64 with a rectangular grid 65 formed by cross-members 66,68 that intersect at right angles to form a plurality of rectangular pockets 70 to improve adhesion to the tooth. The pattern of the bonding base is preferably in the form of a series of square or rectangular pockets that are approximately 0.005 to 0.015 inch in size along at least one side, and typically 0.005 inches deep at the centers of the pockets. The unitary body has an archwire slot 72 formed in the facebow tube 76. In a presently preferred aspect, the archwire slot is formed as a rectangular aperture for receiving an archwire for anchorage and straightening of the tooth. A hook 80 is also preferably provided on the unitary body, for attaching an elastic band, ligature wire, or the like. A channel 82 is also preferably formed in the unitary body adjacent to the archwire slot in the facebow tube, as an aid for threading the archwire through the archwire slot. The buccal tube 60 is also typically used on the molar teeth, such as the molar, and second molar, for straightening and alignment.

In each of the foregoing embodiments, the orthodontic appliance is preferably made from a biocompatible metal alloy designed for strength, hardness, and resistance to corrosion. In one presently preferred aspect of the invention, the biocompatible metal alloy of the orthodontic appliances of the invention is in the Stellite 21 family, with the following percentages, by weight: cobalt 59–69%; chromium 26–30%; and molybdenum 4–8%, with 2% or less of the material comprising trace elements, and nickel present in an amount less than 1%, to be substantially nickel-free according to industry standards, in order to alleviate possible allergic reactions to nickel. The biocompatible metal alloy are injection or press molded into a mold cavity in a powdered state, with a binder, and sintered into the final unitary product. Alternatively, such metals as a 17-4 ph stainless steel, F-75 cobalt chromium alloy, or similar biocompatible metal alloys may also be suitable.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A unitary metal injection molded orthodontic bracket for straightening teeth, comprising:

a unitary metal injection molded body including a bonding base adapted to adhere to a tooth surface, said body having a surface defining an archwire slot adapted for receiving an archwire; and said body being formed from a metal alloy having a composition consisting essentially of cobalt, chromium, and molybdenum, with nickel being present in an amount less than 1% by weight.

2. The unitary metal injection molded orthodontic bracket of claim 1, wherein said composition consists essentially of 59–69% by weight cobalt, 26–30% by weight chromium, 4–8% by weight molybdenum, and 2% or less by weight trace elements.

3. The unitary metal injection molded orthodontic bracket of claim 1, wherein said body further includes a plurality of tiewings.

4. The unitary metal injection molded orthodontic bracket of claim 1, wherein said bonding base has a bonding base pattern in the form of a plurality of rectangular pockets.

5. The unitary metal injection molded orthodontic bracket of claim 4, wherein said pockets are approximately 0.005 to 0.015 inch in size along at least one side, and approximately 0.005 inches deep.

6. The unitary metal injection molded orthodontic bracket of claim 4, wherein said bonding base pattern comprises a plurality of square pockets.

7. A unitary metal injection molded orthodontic appliance, comprising:

a unitary metal injection molded body having a bonding base and a facebow tube for receiving wires for anchorage and straightening of the tooth, said body having a surface defining a primary archwire slot for receiving an archwire for anchorage and straightening of the tooth; and said body being formed from a metal alloy having a composition consisting essentially of cobalt, chromium, and molybdenum, with nickel being present in an amount less than 1% by weight.

8. The unitary metal injection molded orthodontic appliance of claim 7, wherein said composition consists essentially of 59–69% by weight cobalt, 26–30% by weight chromium, 4–8% by weight molybdenum, and 2% or less by weight trace elements.

9. The unitary metal injection molded orthodontic appliance of claim 7, wherein said primary archwire slot includes an auxiliary archwire slot for receiving the archwire.

10. The unitary metal injection molded orthodontic appliance of claim 7, wherein said body further comprises a plurality of tiewings.

11. The unitary metal injection molded orthodontic appliance of claim 7, wherein said bonding base has a bonding base pattern in the form of a plurality of rectangular pockets.

12. The unitary metal injection molded orthodontic appliance of claim 11, wherein said pockets are approximately 0.005 to 0.015 inch in size along at least one side, and approximately 0.005 inches deep.

13. The unitary metal injection molded orthodontic appliance of claim 11, wherein said bonding base pattern comprises a plurality of square pockets.

14. The unitary metal injection molded orthodontic appliance of claim 7, wherein said appliance is adapted for application to first and second molar teeth.

15. The unitary metal injection molded orthodontic appliance of claim 7, wherein said appliance is a buccal tube bracket.

16. The unitary metal injection molded orthodontic appliance of claim 7, wherein said facebow tube has a round aperture for receiving a cylindrical wire.

17. The unitary metal injection molded orthodontic appliance of claim 7, wherein said facebow tube has a rectangular aperture for receiving an archwire.

* * * * *

UNITED STATES PATENT AND TRADEMARK OFFICE
CERTIFICATE OF CORRECTION

PATENT NO. : 6,053,729
DATED : Apr. 25, 2000
INVENTOR(S) : Lindsay W. Brehm, Stephen M. Huff, Chhattar S. Kucheria It is certified that error appears in the above-identified patent and that said Letters Patent is hereby corrected as shown below:

Title page, under "Assignee:", change "Corporation", to read --Organizers--.

Signed and Sealed this

Fifteenth Day of May, 2001

Attest:

NICHOLAS P. GODICI

Attesting Officer     Acting Director of the United States Patent and Trademark Office